(12) United States Patent
Ishikita

(10) Patent No.: US 11,986,586 B2
(45) Date of Patent: May 21, 2024

(54) CATHETER FOR CHEST DRAINAGE AND CHEST DRAINAGE SYSTEM

(71) Applicant: Naoyuki Ishikita, Niigata (JP)

(72) Inventor: Naoyuki Ishikita, Niigata (JP)

( * ) Notice: Subject to any disclaimer, the term of this patent is extended or adjusted under 35 U.S.C. 154(b) by 0 days.

(21) Appl. No.: 17/477,902

(22) Filed: Sep. 17, 2021

(65) Prior Publication Data

US 2023/0093153 A1 Mar. 23, 2023

(51) Int. Cl.
*A61M 1/00* (2006.01)

(52) U.S. Cl.
CPC ............... *A61M 1/84* (2021.05); *A61M 1/85* (2021.05); *A61M 2205/3344* (2013.01); *A61M 2210/1039* (2013.01)

(58) Field of Classification Search
CPC .. A61M 1/84; A61M 1/85; A61M 2205/3344; A61M 2210/1039; A61M 2027/004; A61M 27/00; A61M 2039/0276; A61M 2210/101; A61M 1/61; A61F 5/445; A61F 5/4405
See application file for complete search history.

(56) References Cited

U.S. PATENT DOCUMENTS

| | | | |
|---|---|---|---|
| 3,253,594 A | 5/1966 | Matthews et al. | |
| 4,959,054 A | 9/1990 | Heimke | |
| 8,336,540 B2 * | 12/2012 | Tanaka | A61M 16/0406 |
| | | | 128/205.27 |
| 8,347,881 B2 * | 1/2013 | Tanaka | A61M 16/0429 |
| | | | 128/207.29 |
| 2007/0163598 A1 | 7/2007 | Chang et al. | |
| 2007/0265584 A1 * | 11/2007 | Hickman | A61M 1/3659 |
| | | | 604/288.01 |

(Continued)

FOREIGN PATENT DOCUMENTS

| | | |
|---|---|---|
| JP | 63-181771 A | 7/1988 |
| JP | 2007-190388 A | 8/2007 |

(Continued)

OTHER PUBLICATIONS

Japanese Office Action for Application No. 2020-010421 (dated Aug. 29, 2023) with English language translation thereof.

(Continued)

*Primary Examiner* — Adam Marcetich
*Assistant Examiner* — Rachel O'Connell
(74) *Attorney, Agent, or Firm* — Future IP LLC; Tomoko Nakajima

(57) ABSTRACT

To reduce the suffering of the patient and enable easier removal of excess fluid such as pleural effusion fluid from the chest space, the disclosure provides a catheter for chest drainage intended for removal of excess fluid from a chest space of a living body and to be placed in the living body in such a manner as to extend from an inside of the chest space to an outside of the living body. The catheter includes a passage member formed of a flexible sheet and having a passage through which the excess fluid is to be drained, and an indwelling member formed of an elastic body and provided at a proximal end of the passage member. The indwelling member has an inlet that allows the excess fluid to flow through. The indwelling member includes a retaining portion spreading in a flange shape and being retainable at a chest wall.

19 Claims, 6 Drawing Sheets

(56) References Cited

U.S. PATENT DOCUMENTS

| | | | |
|---|---|---|---|
| 2009/0209856 A1 | 8/2009 | Tanaka et al. | |
| 2010/0122699 A1 | 5/2010 | Birnkrant | |
| 2010/0204707 A1* | 8/2010 | Tanaka | A61M 39/0247 |
| | | | 606/108 |
| 2013/0253456 A1* | 9/2013 | Friske | A61F 5/4407 |
| | | | 604/332 |
| 2017/0007749 A1* | 1/2017 | Walti | A61M 1/743 |
| 2019/0381220 A1* | 12/2019 | Locke | A61M 1/74 |
| 2020/0253633 A1* | 8/2020 | Obst | A61B 17/3417 |
| 2021/0187257 A1* | 6/2021 | Khanna | A61M 1/0011 |

FOREIGN PATENT DOCUMENTS

| | | |
|---|---|---|
| JP | 2008-206734 A | 9/2008 |
| JP | 2015-013184 A | 1/2015 |
| JP | 2015-181511 A | 10/2015 |
| JP | 2017-506936 A | 3/2017 |
| JP | 2017-532074 A | 11/2017 |
| WO | WO2016/054051 A1 | 4/2016 |

OTHER PUBLICATIONS

Japanese Decision to Grant a Patent for Application No. 2020-010421 (dated Nov. 7, 2023) with English language translation thereof.

\* cited by examiner

PRIOR ART

CATHETER FOR CHEST DRAINAGE AND CHEST DRAINAGE SYSTEM

BACKGROUND OF THE INVENTION

1. Field of the Invention

The present disclosure relates to a catheter for chest drainage, a chest drainage system, and a chest drainage method.

2. Description of the Related Art

Chest drainage is one of the medical techniques of draining excess fluid such as excess air or body fluid (pleural effusion fluid or blood, for example) accumulated in the chest space of a living body due to some disease to the outside of the living body. In chest drainage, a tube is inserted into the chest space through an incision made into the chest wall, and the excess fluid in the chest space is drained through the tube. Treatment with chest drainage is performed in the following cases, for example: a case where pleural effusion fluid accumulated in the chest space due to lung cancer or pleurisy is to be removed; and a case where air leaked from a punctured lung and accumulated in the chest space, causing pneumothorax, is to be removed from the chest space. Known devices for performing chest drainage include, for example, a chest drainage device disclosed by Japanese Unexamined Patent Application Publication (Translation of PCT Application) No. 2017-506936, in which a drainage tube inserted into the chest space is connected to a fluid collecting container, and fluid such as pleural effusion fluid is drained to the outside of the living body by suction with a negative pressure.

SUMMARY OF THE INVENTION

Drainage tubes are made of hard resin and have a cylindrical shape. Such a drainage tube inserted into a patient tends to give pain to the patient even at a slight movement of the drainage tube, from which the patient persistently suffers. Moreover, a skillful technique is required to insert a drainage tube into an appropriate site of the patient's chest space, fix the drainage tube, and suction the fluid such as pleural effusion fluid from the chest space by generating a negative pressure.

The present disclosure has been conceived in view of the above problems and provides a solution that reduces the suffering of the patient and enables easier removal of excess fluid such as pleural effusion fluid from the chest space.

A first aspect of the present disclosure provides a catheter for chest drainage intended for removal of excess fluid from a chest space of a living body and to be placed in the living body in such a manner as to extend from an inside of the chest space to an outside of the living body. The catheter includes a passage member formed of a flexible sheet and having a passage through which the excess fluid is to be drained, and an indwelling member formed of an elastic body and provided at a proximal end of the passage member. The indwelling member has an inlet that allows the excess fluid to flow through. The indwelling member includes a retaining portion spreading in a flange shape and being retainable at a chest wall.

According to the first aspect of the present disclosure, it is easy to place the catheter for chest drainage in the living body, which facilitates the removal of the excess fluid such as pleural effusion fluid from the chest space.

In the first aspect of the present disclosure, the indwelling member may have a groove in a region overlapping at least the inlet.

In such a configuration, even if the indwelling member is covered by the inflated lungs, the excess fluid is introduced into the inlet through the groove, which facilitates the assured draining of the excess fluid in the chest space to the outside.

In the first aspect of the present disclosure, the indwelling member may further include a connecting portion connected to the proximal end of the passage member, and the retaining portion may spread in the flange shape with respect to the connecting portion.

In such a configuration, the connecting portion serves as a check valve that prevents foreign matter, such as gas, liquid, or a solid body, from entering the inlet from the outside of the living body.

In the first aspect of the present disclosure, the passage member may be formed of a pair of flexible sheets that are connected to each other at both lateral ends, a proximal end of each of the flexible sheets may be connected to the connecting portion, the inlet may open when the excess fluid flows into the groove, the connecting portion may undergo elastic deformation from a flat shape into a tubular shape when the inlet opens, and the passage may open between the lateral ends of the flexible sheets when the connecting portion undergoes the elastic deformation.

In such a configuration, the catheter for chest drainage is provided as a minimally invasive chest drainage catheter that gives less pain to the patient and with which the excess fluid such as pleural effusion fluid is efficiently removable from the chest space.

In the first aspect of the present disclosure, the indwelling member may be made of silicone rubber.

In such a configuration, an operation of opening or closing the inlet and an operation of retaining the retaining portion at the thorax are achieved by the elastic deformation.

In the first aspect of the present disclosure, the flexible sheet forming the passage member may be a resin film.

In such a configuration, since the passage member is made of a resin film, which is not hard, the catheter for chest drainage is provided as a minimally invasive chest drainage catheter that gives less pain to the patient having the catheter placed.

Another aspect of the present disclosure provides a chest drainage system configured to remove excess fluid from a chest space of a living body. The system includes the catheter for chest drainage configured as any of the above, and a gas supplying unit configured to generate a positive pressure in lungs of the living body by supplying gas into the lungs.

According to another aspect, the excess fluid such as pleural effusion fluid is easily removable from the chest space simply by placing the catheter for chest drainage such that the catheter extends from the inside of the chest space of the living body and through the chest wall and by applying a positive pressure to the lungs.

According to the present disclosure, the suffering of the patient is reduced, and easier removal of excess fluid such as pleural effusion fluid from the chest space is achieved.

DESCRIPTION OF THE PREFERRED EMBODIMENTS

A preferred embodiment according to the aspects of the present disclosure will now be described in detail. The following embodiment does not unreasonably limit the scope of the present invention defined by the appended claims. It is not necessarily true that all of the configurations to be described in the following embodiment are essential as the solution provided by the present invention.

Figure 1:
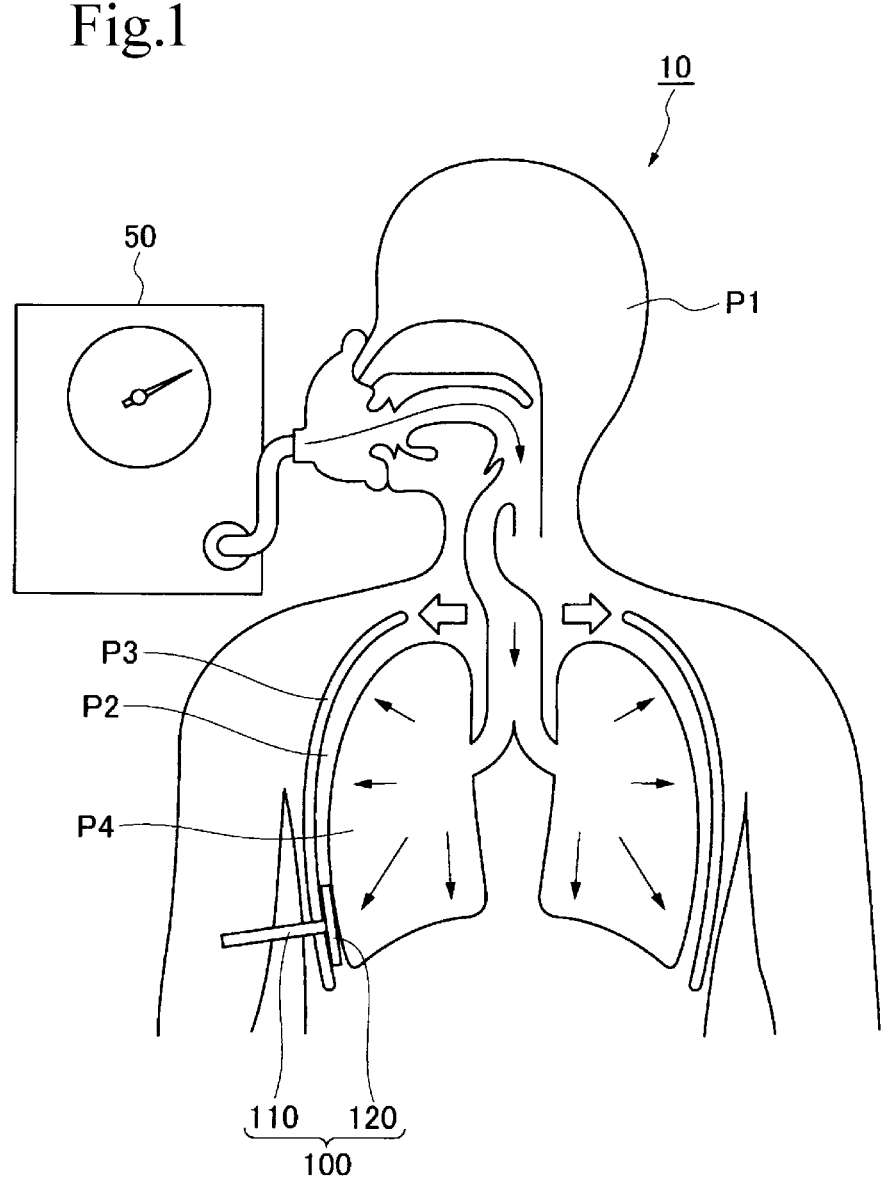
FIG. 1 is a block diagram schematically illustrating a chest drainage system according to an embodiment.

A configuration of a chest drainage system 10 according to an embodiment will first be described with reference to relevant drawings. FIG. 1 is a block diagram schematically illustrating the chest drainage system 10 according to the present embodiment.

The chest drainage system 10 is used in performing chest drainage, in which excess fluid such as pleural effusion fluid in a chest space P2 is drained through a chest drainage catheter 100, which is inserted into the chest space P2 through an incision made into a chest wall P3 of a patient P1. As illustrated in FIG. 1, the chest drainage system 10 according to the present embodiment includes the chest drainage catheter 100 and a gas supplying unit 50.

The chest drainage catheter 100 is to be placed in such a manner as to extend from the inside of the chest space P2 of the patient P1 to the outside of the body of the patient P1, so that excess fluid such as pleural effusion fluid is removed from the chest space P2. The chest drainage catheter 100 includes a passage member 110 and an indwelling member 120. The passage member 110 has a passage through which the excess fluid is to be drained. The indwelling member 120 is provided at the proximal end of the passage member 110 and is placed in the body of the patient P1 in such a manner as to be retained at the chest wall P3. Details of the chest drainage catheter 100 will be described separately below.

The gas supplying unit 50 supplies gas into lungs P4 of the patient P1, which is the living body, thereby generating a positive pressure in the lungs P4. The gas supplying unit 50 according to the present embodiment may be any of the following: a respiratory care device with a mechanical insufflation-exsufflation function, an airbag with a function of supplying air or oxygen, a disposable respirator, and the like.

The chest drainage system 10 according to the present embodiment is used as follows. The chest drainage catheter 100 is placed in the patient P1 in such a manner as to extend from the inside of the chest space P2 of the patient P1 to the outside of the body of the patient P1. Then, intermittent positive pressure ventilation (IPPV) is performed by using the gas supplying unit 50. The gas supplying unit 50 generates a positive pressure on the outside of the living body to produce a pressure difference and thus feeds air into the lungs P4. Consequently, the excess fluid is naturally drained through the chest drainage catheter 100. The excess fluid thus drained is, for example, absorbed by a water-absorbing pad or the like. A specific method of chest drainage performed by using the chest drainage system 10 according to the present embodiment will be described separately below.

Figure 2:
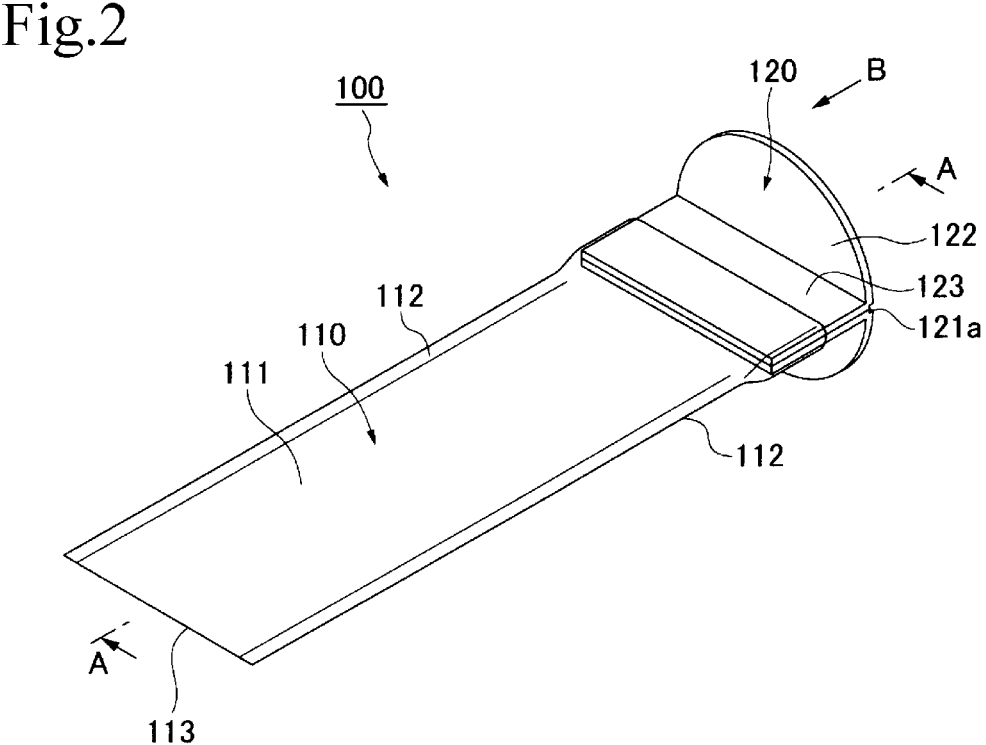
FIG. 2 is a schematic perspective view of a catheter for chest drainage according to the embodiment.
Figure 3:
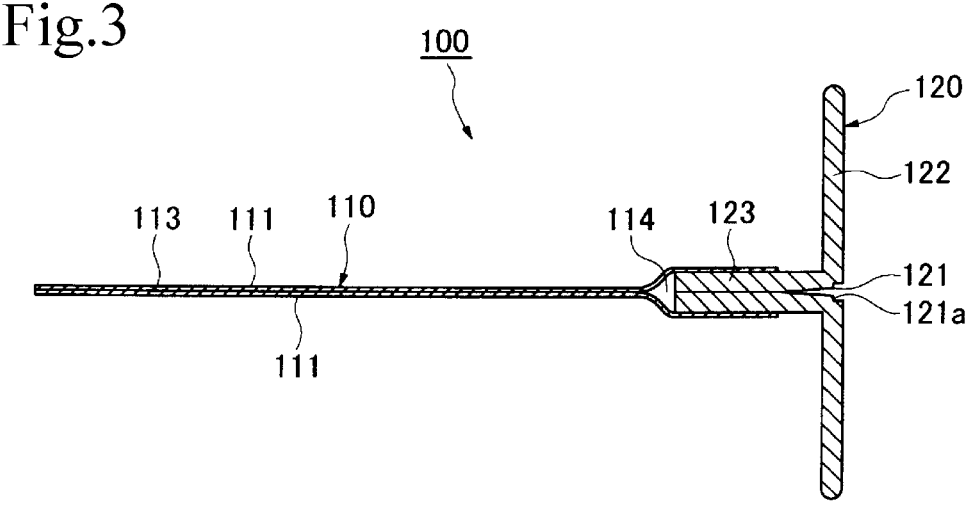
FIG. 3 is a sectional view taken along line III-III of FIG. 2.
Figure 4A:
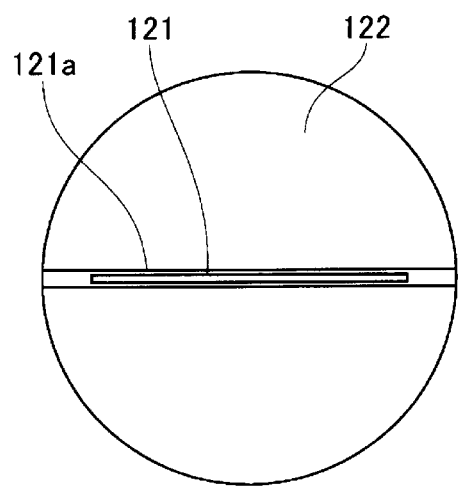
FIG. 4A is a front view of the catheter for chest drainage, seen in direction B illustrated in FIG. 2.
Figure 4B:
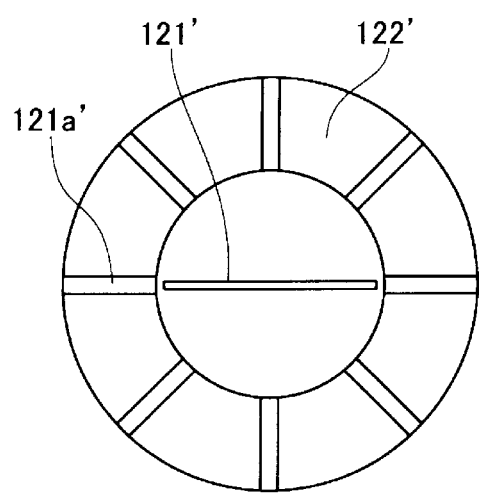
FIG. 4B is a front view of a catheter for chest drainage according to a modification, seen in direction B illustrated in FIG. 2.

Details of the chest drainage catheter 100 according to the present embodiment will now be described with reference to relevant drawings. FIG. 2 is a schematic perspective view of the chest drainage catheter 100 according to the present embodiment. FIG. 3 is a sectional view of the chest drainage catheter 100 according to the present embodiment. FIG. 4A is a front view of the chest drainage catheter 100 according to the present embodiment, illustrating a retaining portion thereof. FIG. 4B is a front view of a chest drainage catheter 100 according to a modification of the present embodiment, illustrating a retaining portion thereof.

The chest drainage catheter 100 is used in performing chest drainage, in which excess fluid such as pleural effusion fluid in the chest space P2 is drained. The chest drainage catheter 100 serves as a member through which the excess fluid is to be drained to the outside of a living body. The chest drainage catheter 100 includes the passage member 110 and the indwelling member 120.

The passage member 110 is formed of a pair of ribbon-shaped flexible sheets 111, which are soft resin films made of polyvinyl chloride or the like. The passage member 110 serves as a drain passage through which the excess fluid in the chest space P2 is to be drained. As illustrated in FIG. 2, the pair of flexible sheets 111 forming the passage member 110 are connected to each other at both lateral ends 112 thereof. A passage 113 through which the excess fluid is to be drained is defined between the lateral ends 112. The passage member 110 has a length of, for example, about 5 to 15 cm and a width of, for example, about 1.0 to 1.5 cm.

As illustrated in FIG. 3, the passage member 110 is connected to a connecting portion 123, which is included in the indwelling member 120, at the proximal ends of the flexible sheets 111. At normal times, the passage member 110 is collapsed in a flat sheet-like shape. Specifically, at normal times, the pair of ribbon-shaped flexible sheets 111 forming the passage member 110 are in surface contact with each other. At times of drainage of the excess fluid, the excess fluid flows into the passage member 110 from between the proximal ends of the flexible sheets 111 and opens the passage 113 defined between the lateral ends 112 of the flexible sheets 111. At normal times, since the pair of ribbon-shaped flexible sheets 111 forming the passage member 110 are in contact with each other over the entirety thereof in the lengthwise direction, foreign matter is less likely to enter the passage member 110 from the distal end (the end from which the excess fluid is discharged).

The indwelling member 120 is a rubber elastic body made of silicone rubber or the like and has a function of retaining the proximal end of the chest drainage catheter 100 in the chest space P2. As illustrated in FIGS. 2 and 3, the indwelling member 120 according to the present embodiment is provided at the proximal end of the passage member 110 and includes a retaining portion 122, which has a flange shape, and the connecting portion 123, which has a plate shape. The retaining portion 122 and the connecting portion 123 form an integral body as a whole. As illustrated in FIG. 3, the indwelling member 120 according to the present embodiment has an inlet 121 in the center of the retaining portion 122. As illustrated in FIG. 3, the inlet 121 has a wedge-like sectional shape that is tapered toward the distal end of the connecting portion 123 so that the excess fluid is smoothly introduced into the passage member 110.

The retaining portion 122 spreads in a flange shape with respect to the connecting portion 123. The retaining portion 122 is a disc-shaped rubber elastic body and serves as a retaining member to be retained at the chest wall P3 when the chest drainage catheter 100 is placed in the patient P1. At normal times, the retaining portion 122 extends perpendicularly to the plate-shaped connecting portion 123. To allow the chest drainage catheter 100 to be placed in the patient P1, the retaining portion 122 is elastically bendable in such a manner as to be aligned with the connecting portion 123 in a straight line. In the present embodiment, the retaining portion 122 has a disc shape, which is isotropic. Therefore, regardless of the orientation of the retaining portion 122 at the time of insertion, the retaining portion 122 is assuredly retained at the chest wall P3. The shape of the retaining portion 122 is not limited to a disc shape and may be any other shape, such as a polygonal shape or an oval shape.

As illustrated in FIG. 4A, the retaining portion 122 has the inlet 121 in the center thereof. The inlet 121 has a slit shape extending from the back face of the retaining portion 122 and allows the excess fluid to flow therethrough. The retaining portion 122 further has a groove 121a in the back face thereof. The groove 121a is provided in a region overlapping the inlet 121 so that the excess fluid is smoothly introduced into the inlet 121. The groove 121a only needs to be provided in a region overlapping at least the inlet 121 and is not limited to the one illustrated in FIG. 4A. For example, a retaining portion 122' illustrated in FIG. 4B may alternatively be employed, in which a plurality of grooves 121a' are provided in the back face of the retaining portion 122' and are arranged radially around an inlet 121'.

The connecting portion 123 is a plate-shaped elastic body and connects the passage member 110 and the inlet 121 of the indwelling member 120 to each other. The connecting portion 123 is formed of a pair of plate-shaped elastic bodies, which are connected to the proximal ends of the respective flexible sheets 111 forming the passage member 110. The pair of elastic bodies are connected to each other at both lateral ends thereof, thereby forming the connecting portion 123. The connecting portion 123 is not limited to a pair of plate-shaped elastic bodies that are connected to each other. The connecting portion 123 may be provided in any other form, such as the form of a flat tube.

The connecting portion 123 has a passage that opens elastically when the inlet 121 opens. The excess fluid passed through the inlet 121 flows through the passage of the connecting portion 123. The connecting portion 123 also serves as a check valve that prevents foreign matter or the like from entering the living body from the outside of the living body. In the present embodiment, the indwelling member 120 includes the connecting portion 123. Alternatively, another embodiment may be employed in which the proximal end of the passage member 110 is directly connected to the retaining portion 122 having the inlet 121.

In the present embodiment, as described above, the passage member 110 is formed of the pair of flexible sheets 111 that are connected to each other at the lateral ends 112 thereof, and the connecting portion 123 is connected to the proximal ends of the flexible sheets 111. The above plate-shaped bodies forming the connecting portion 123 are each thicker than the flexible sheets 111 forming the passage member 110. Therefore, as illustrated in FIG. 3, a space 114 is provided at the proximal end of the passage member 110.

When the excess fluid flows into the groove 121a of the retaining portion 122, the inlet 121 opens. With the opening of the inlet 121, the connecting portion 123 undergoes elastic deformation from a flat shape into a tubular shape, whereby the passage in the connecting portion 123 opens. With the elastic deformation of the connecting portion 123, the passage 113 defined between the lateral ends 112 of the flexible sheets 111 opens. In this process, since there is the space 114 at the proximal end of the passage member 110, the excess fluid passed through the inlet 121 and the connecting portion 123 is naturally received by the space 114 provided between the proximal ends of the flexible sheets 111. Therefore, the passage 113 that has been closed between the flexible sheets 111 is smoothly opened. That is, the space 114 serves as an introduction port that introduces the flow of the excess fluid. If the inlet 121 itself has such a shape as to smoothly introduce the excess fluid thereinto, the space 114 may not necessarily be provided. In that case, the flexible sheets 111 may be closely in contact with the distal end of the connecting portion 123 of the indwelling member 120 having the inlet 121.

Figure 5:
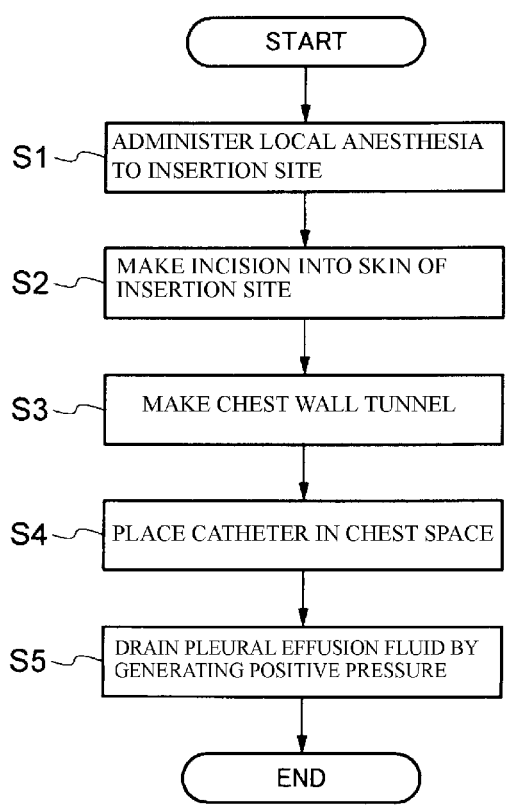
FIG. 5 is a flowchart illustrating an operation of draining excess fluid (a minimally invasive positive-pressure chest drainage method) that is performed by using a chest drainage system according to the embodiment.
Figure 6A:
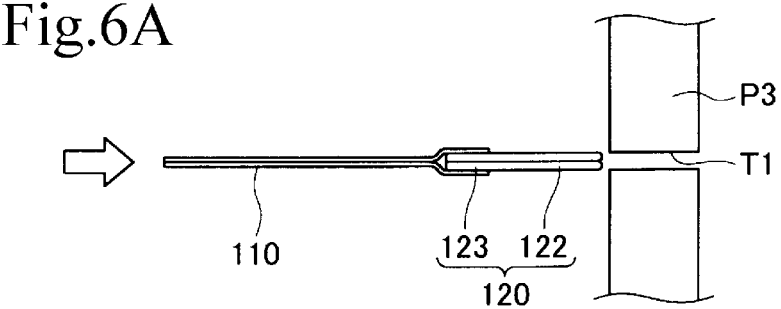
FIG. 6A to 6C illustrate an operation of placing the catheter for chest drainage according to the embodiment in a living body.
Figure 6B:
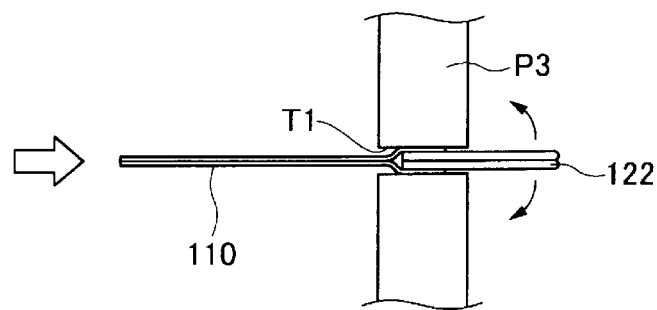
Figure 6C:
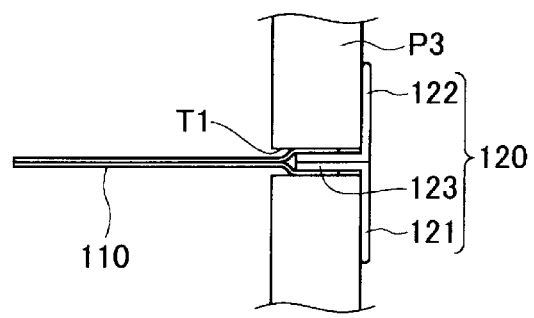

Now, an operation of draining the excess fluid by using the chest drainage system 10 according to the present embodiment and a method thereof (a chest drainage method, specifically a minimally invasive positive-pressure chest drainage method) will be described with reference to relevant drawings. FIG. 5 is a flowchart illustrating an operation of draining the excess fluid that is performed by using the chest drainage system 10 according to the present embodiment. FIG. 6A to 6C illustrate an operation of placing the chest drainage catheter 100 according to the present embodiment in a living body.

The chest drainage system 10 according to the present embodiment is used in performing treatment with chest drainage, in which excess fluid such as air or body fluid (pleural effusion fluid or blood, for example) accumulated in the chest space of a living body due to some disease is drained to the outside of the living body. Treatment with chest drainage using the chest drainage system 10 according to the present embodiment is performed in the following cases, for example: a case where pleural effusion fluid accumulated in the chest space due to lung cancer or pleurisy is to be removed; and a case where air leaked from a punctured lung and accumulated in the chest space, causing pneumothorax, is to be removed from the chest space.

The chest drainage catheter 100 is placed in the patient P1 as follows. First, local anesthesia is administered to an insertion site where the chest drainage catheter 100 is to be inserted (step S1). After local anesthesia is administered, an incision with a diameter of about 1 cm, for example, is made into the skin of the insertion site with a scalpel or the like (step S2). Then, a chest wall tunnel T1 into which the chest drainage catheter 100 is to be inserted is bluntly made with a pair of forceps, a pair of tweezers, the little finger, or the like (step S3).

After the chest wall tunnel T1 is made, the chest drainage catheter 100 is pinched with a pair of forceps or the like and is placed in the chest space (step S4). In the present embodiment, the indwelling member 120 of the chest drainage catheter 100 is an integral body made of an elastic material such as silicone rubber. Therefore, as illustrated in FIG. 6A, the retaining portion 122 is first pinched with a pair of forceps or the like (not illustrated) in such a manner as to be elastically folded to extend in the same direction as the connecting portion 123. Then, the retaining portion 122 is inserted into the chest wall tunnel T1.

After the entirety of the retaining portion 122 comes out of the chest wall tunnel T1, as illustrated in FIG. 6B, the pair of forceps or the like is removed from the retaining portion 122. Accordingly, as illustrated in FIG. 6C, the retaining portion 122 expands perpendicularly to the connecting portion 123 with the restoring force exerted by the rubber elastic bodies forming the retaining portion 122, whereby the retaining portion 122 is retained at the chest wall P3. Thus, the operation of placing the chest drainage catheter 100 in the living body is complete.

After the chest drainage catheter 100 is placed in the living body, gas is supplied from the gas supplying unit 50 into the lungs P4 of the patient P1 to inflate the lungs P4 with a positive pressure. Thus, the pressure in the chest space P2 is increased, whereby the excess fluid such as pleural effusion fluid is drained to the outside of the living body (step S5).

In the present embodiment, as described above, after the chest drainage catheter 100 is placed in the patient P1, the lungs P4 are inflated with a positive pressure generated by the gas supplying unit 50, whereby the excess fluid such as pleural effusion fluid in the chest space P2 is drained to the outside naturally under the weight of the excess fluid itself (the gravitational force acting on the excess fluid). That is, the excess fluid such as pleural effusion fluid is easily removable from the chest space P2 simply by placing the chest drainage catheter 100 such that the catheter 100 extends from the inside of the chest space P2 of the living body and through the chest wall P3 and by applying a positive pressure to the lungs P4.

Figure 7A:
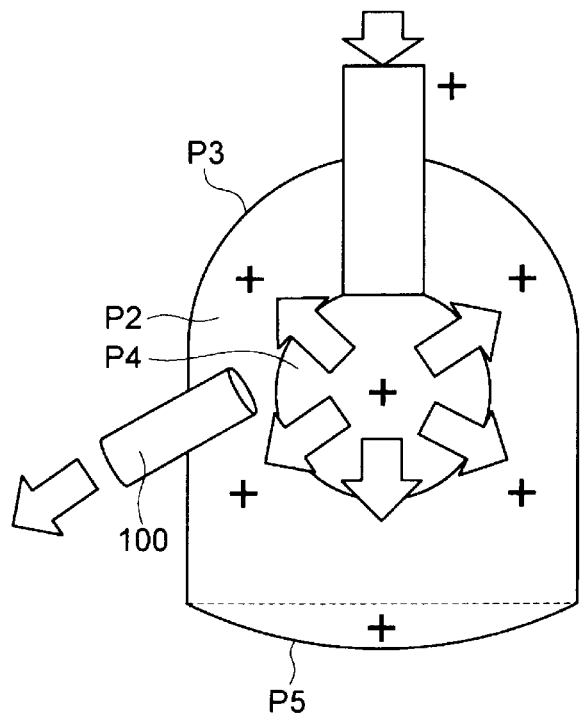
FIG. 7A illustrates the operation of draining excess fluid that is performed by using the chest drainage system according to the embodiment.
Figure 7B:
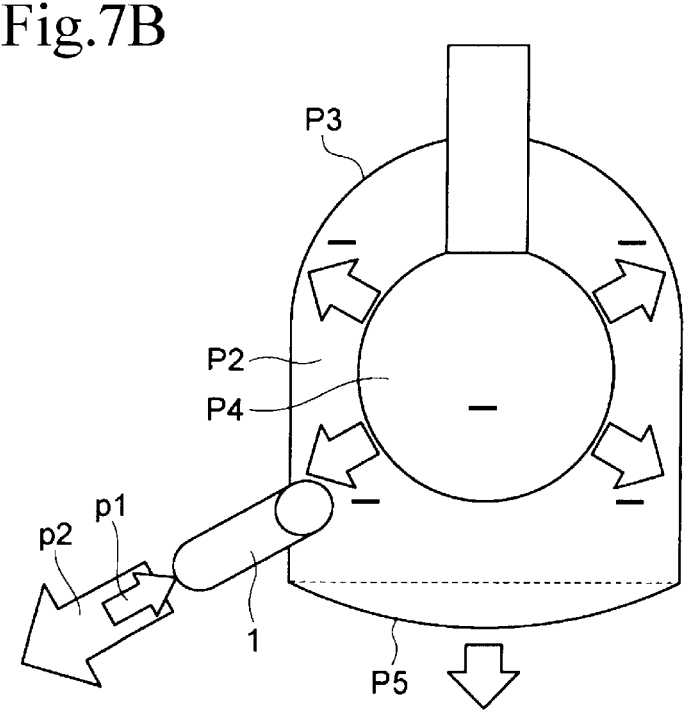
FIG. 7B illustrates an operation of draining excess fluid that is performed by generating a negative pressure, according to a comparative embodiment.

Now, advantageous effects produced by the chest drainage catheter 100 and the chest drainage system 10 according to the present embodiment will be described. FIG. 7A illustrates the operation of draining the excess fluid that is performed by using the chest drainage system 10 according to the present embodiment. FIG. 7B illustrates an operation of draining the excess fluid that is performed by generating a negative pressure, according to a comparative embodiment. In each of FIGS. 7A and 7B, the living body in which the chest drainage catheter 100 or a chest drainage catheter 1 is placed is illustrated schematically.

The chest drainage system 10 according to the present embodiment enables a "minimally invasive positive-pressure chest drainage method" through positive pressure ventilation performed by using the chest drainage catheter 100, which is softer and shorter than known ones. Specifically, as illustrated in FIG. 7A, the chest drainage catheter 100 is placed in the living body in such a manner as to extend from the inside of the chest space P2 through the chest wall P3 to the outside of the living body, and a positive pressure is then applied to the lungs P4, whereby the lungs P4 are inflated, which increases the pressure in the chest space P2.

Therefore, with the chest drainage system 10 according to the present embodiment, while a diaphragm P5 is displaced outward, excess fluid such as pleural effusion fluid or air (in the case of pneumothorax) of an amount corresponding to the amount of inflation of the lungs P4 is forced to be discharged. Thus, the excess fluid is naturally drained from the chest space P2 to the outside of the living body through the chest drainage catheter 100. Furthermore, in the present embodiment, since the positive pressure applied to the chest space P2 causes the excess fluid to be naturally drained under its own weight through the chest drainage catheter 100, minimally invasive chest drainage of excess fluid is achieved even with the passage member 110 that is formed of thin, soft sheets.

Furthermore, in the present embodiment, since the positive pressure applied to the chest space P2 causes the excess fluid to be naturally drained through the chest drainage catheter 100, the site where the chest drainage catheter 100 is to be placed is not strictly limited and is settable to a desired position with a certain degree of freedom, as long as the chest drainage catheter 100 is placed in such a manner as to extend from the inside of the chest space P2 and through the chest wall P3. That is, the chest drainage catheter 100 is easily placeable for chest drainage, with no skillful technique. Note that the chest drainage catheter 100 according to the present embodiment is preferably inserted from the precordium, in view of efficient performance of maintenance work such as absorption of the drained excess fluid with a water-absorbing pad, or refeeding of albumin into the blood by intravenous administration to be performed after filtration of the excess fluid that is aseptically stored in a bag.

In contrast, in known negative-pressure chest drainage, which is taken as a comparative embodiment illustrated in FIG. 7B, the chest space P2 is physiologically subjected to a negative pressure. Therefore, simply inserting a catheter 1 into an incision made into the chest wall P3 does not cause the excess fluid such as pleural effusion fluid in the chest space P2 to be naturally drained. Moreover, to assuredly drain the excess fluid such as pleural effusion fluid in the chest space P2, the catheter 1 needs to be placed at the lowest site in the chest space P2. That is, the site where the catheter 1 is to be placed is limited.

In negative-pressure chest drainage, considering the safety of the patient P1, the catheter 1 needs to be inserted after the site where excess fluid such as pleural effusion fluid is present and the site where the catheter 1 is safely insertable are located through an examination such as echography, a chest X-ray examination, or chest computed tomography (CT). Therefore, as a prevention of serious complications such as pneumothorax or bleeding as well, known chest drainage requires a skillful technique of assuredly locating the site where excess fluid to be suctioned is present and then placing the catheter 1 in the located site.

Furthermore, in negative-pressure chest drainage, since the chest space P2 is physiologically subjected to a negative pressure, simply making an incision into the chest wall P3 of the living body does not cause the excess fluid such as pleural effusion fluid to be drained. Therefore, to remove the excess fluid, a suction mechanism such as a pump that suctions the excess fluid is required. Specifically, in negative-pressure chest drainage, the diaphragm P5 is pulled downward, increasing the volume of the chest space P2, whereby a negative pressure corresponding to the volume increase is generated in the chest space P2. Therefore, as illustrated in FIG. 7B, excess fluid cannot be removed by suction unless a negative pressure exerting a pulling force p2 that is greater than a suction force p1 acting toward the chest space P2 is applied. Hence, negative-pressure chest drainage requires a large-scale negative-pressure water sealing device including a chest drainage bag. Consequently, the patient P1 connected to such a device is bound by many restrictions on activities of daily living, resulting in unsatisfactory quality of life (QOL).

Moreover, in negative-pressure chest drainage, if the tube forming the catheter 1 is soft, the catheter 1 easily collapses. Furthermore, if the tube forming the catheter 1 is thin, the catheter 1 is easily clogged. Therefore, the catheter 1 for chest drainage is formed of a drainage tube, which is a cylindrical member made of hard resin and having a satisfactorily large diameter. Such a catheter 1 inserted into the patient P1 tends to give pain to the patient P1 at every movement of the catheter 1, from which the patient P1 persistently suffers.

In contrast, the chest drainage system 10 according to the present embodiment applies a positive pressure to the lungs P4, whereby the excess fluid in the chest space P2 is naturally drained through the chest drainage catheter 100. Therefore, unlike the case of negative-pressure chest drainage, there is no need to apply suction for removing the excess fluid through the chest drainage catheter 100, which simplifies the system for performing chest drainage and reduces the restrictions on activities of daily living of the patient P1, providing satisfactory QOL.

In the chest drainage system 10 according to the present embodiment, the passage member 110 is formed of the flexible sheets 111 that are soft resin films, and the excess fluid is drainable to the outside of the living body through the chest drainage catheter 100 even if the diameter of the passage member 110 is small. Therefore, minimally invasive chest drainage that reduces the suffering of the patient P1 having the chest drainage catheter 100 placed is achieved. Furthermore, since the application of the chest drainage system 10 and the chest drainage catheter 100 according to the present embodiment enables chest drainage with minimum equipment, the chest drainage system 10 and the chest drainage catheter 100 are effectively utilized at times of emergency of disaster or in developing countries with insufficient supply of medical equipment.

The chest drainage catheter 100 according to the present embodiment includes the passage member 110 in the form of thin films, and the indwelling member 120 in the form of a rubber elastic body made of silicone rubber or the like. Therefore, it is easy to place the chest drainage catheter 100 in the living body, which facilitates the removal of the excess fluid such as pleural effusion fluid from the chest space P2.

Furthermore, in the chest drainage catheter 100 according to the present embodiment, the passage member 110 is formed of the flexible sheets 111 that are soft and thin, and the indwelling member 120 is formed of a rubber elastic body made of silicone rubber or the like. Therefore, when the passage member 110 is subjected to a negative pressure, the passage 113 is closed, making it difficult for gas or liquid or foreign matter such as a solid substance to enter the living body from the outside. That is, the passage member 110 serves as a check valve. On the other hand, the indwelling member 120 includes the connecting portion 123 formed of a leaf spring made of an elastic material. Therefore, when the indwelling member 120 is subjected to a negative pressure, the passage at the distal end of the connecting portion 123 is closed, making it difficult for foreign matter to enter the living body from the outside. That is, the indwelling member 120 also serves as a check valve.

In the present embodiment, the retaining portion 122 of the indwelling member 120 has in the back face thereof the groove 121a in a region overlapping at least the inlet 121. Therefore, the excess fluid to be drained is smoothly introduced into the inlet 121 through the groove 121a. Even if the retaining portion 122 of the indwelling member 120 is covered by the inflated lungs P4, the excess fluid is introduced into the inlet 121 through the groove 121a, which facilitates the assured draining of the excess fluid in the chest space P2 to the outside.

In the present embodiment, the indwelling member 120 is made of silicone rubber. Therefore, the operation of opening or closing the inlet 121 and the operation of retaining the retaining portion 122 at the thorax are easily achieved by the elastic deformation. Furthermore, the flexible sheets 111 forming the passage member 110 are resin films. That is, the passage member 110 is made of resin films, which are soft, not hard. Therefore, the chest drainage catheter 100 is provided as a minimally invasive chest drainage catheter that gives less pain to the patient having the passage member 110 placed.

In the present embodiment, since the flexible sheets 111 forming the passage member 110 are soft resin films, a portion of the passage member 110 that is on the outside of the living body can be suitably laid along the body of the patient P1. Therefore, the QOL of the patient P1 is improved. Furthermore, since the flexible sheets 111 forming the passage member 110 are soft resin films, the passage member 110 is easy to change the length thereof to a desired length (about 5 to 15 cm, for example) so as to fit the body of the patient P1. That is, the chest drainage catheter 100 is easy to handle.

While an embodiment has been described in detail above, it is considered to be easy for those skilled in the art to understand that various modifications can be made to the above embodiment without substantially departing from the novel configuration and advantageous effects of the present invention. Therefore, such modifications are all included in the scope of the present invention.

For example, any term that is used in this specification or the accompanying drawings at least once together with any different terms having wider or the same meanings is exchangeable with any of such different terms in any part of this specification or the drawings. Furthermore, the configurations, operations, methods, and techniques regarding the chest drainage catheter and the chest drainage system are not limited to those described in the above embodiment, and various modifications can be made thereto.

What is claimed is:

1. A catheter for chest drainage intended for removal of excess fluid from a chest space of a living body and to be placed in the living body in such a manner as to extend from an inside of the chest space to an outside of the living body, the catheter comprising:
   a passage member having a passage through which the excess fluid is to be drained; and
   an indwelling member provided at a proximal end of the passage member, the indwelling member
      having an inlet that allows the excess fluid to flow through, and
      a retaining portion having a flange shape and a plate shape facing perpendicular to the passage member at normal times,
   wherein the passage member is collapsed in a flat sheet-like shape at normal times when the passage member is not used to drain the excess fluid,
   wherein the retaining portion is formed of an elastic body and is elastically bent to face in a horizontal direction with respect to the passage member and elastically foldable into a sheet while being inserted into the living body, and spreads in a flange shape perpendicularly with respect to the passage member with restoring force exerted by the rubber elastic body forming the retaining portion after being inserted into the living body and is retainable at a chest wall.

2. The catheter for chest drainage according to claim 1, wherein the indwelling member has a groove in a region overlapping at least the inlet.

3. The catheter for chest drainage according to claim 1, wherein the indwelling member further includes a connecting portion connected to the proximal end of the passage member, and
wherein the retaining portion spreads in the flange shape with respect to the connecting portion.

4. The catheter for chest drainage according to claim 2, wherein the indwelling member further includes a connecting portion connected to the proximal end of the passage member, and
wherein the retaining portion spreads in the flange shape with respect to the connecting portion.

5. The catheter for chest drainage according to claim 1, wherein the indwelling member is made of silicone rubber.

6. The chest drainage system configured to remove the excess fluid from the chest space of the living body, the system comprising:
the catheter for chest drainage according to claim 1; and
a gas supplying unit configured to generate a positive pressure in lungs of the living body by supplying gas into the lungs.

7. The catheter for chest drainage according to claim 3, wherein a space is provided on the proximal end of the passage member.

8. The catheter for chest drainage according to claim 3, wherein the inlet has a wedge-like sectional shape that is tapered toward the distal end of the connecting portion.

9. The catheter for chest drainage according to claim 1, wherein the retaining portion is disc-shaped.

10. The catheter for chest drainage according to claim 2, wherein the groove is provided in a region overlapping the inlet so that the excess fluid is smoothly introduced into the inlet.

11. The chest drainage method to remove the excess fluid from the chest space of the living body, the method comprising:
attaching the catheter according to claim 1 such that the catheter extends from the inside of the chest space of the living body and through the chest wall, and
draining the excess fluid from the chest space to the outside of the living body through the catheter by applying a positive pressure to lungs.

12. The catheter for chest drainage according to claim 1, wherein the passage member is formed of a pair of flexible sheets.

13. The catheter for chest drainage according to claim 12, wherein the indwelling member further includes a connecting portion connected to the proximal end of the passage member,
wherein the proximal end of each of the pair of flexible sheets is connected to the connecting portion,
wherein the inlet opens when the excess fluid flows into the groove,
wherein the connecting portion undergoes elastic deformation from a flat shape into a tubular shape when the inlet opens, and
wherein the passage opens between the lateral ends of the pair of flexible sheets when the connecting portion undergoes the elastic deformation.

14. The catheter for chest drainage according to claim 12, wherein the pair of flexible sheets forming the passage member is a resin film.

15. The catheter for chest drainage according to claim 12, wherein the pair of flexible sheets is flat at normal times when the passage member is not used to drain the excess fluid.

16. The catheter for chest drainage according to claim 12, wherein the proximal end of the pair of flexible sheets and the indwelling member are to be inserted into the living body.

17. The catheter for chest drainage according to claim 4, wherein a space is provided on the proximal end of the passage member.

18. The catheter for chest drainage according to claim 4, wherein the inlet has a wedge-like sectional shape that is tapered toward the distal end of the connecting portion.

19. The catheter for chest drainage according to claim 1, wherein passage member has a space provided on the proximal end of the passage member, the space serves as an introduction port that introduces a flow of the excess fluid, and the space is tapered toward a distal end side.

* * * * *